US00RE38921E

(19) United States
(12) Reissued Patent
Ohashi et al.

(10) Patent Number: US RE38,921 E
(45) Date of Reissued Patent: Dec. 13, 2005

(54) PHENOXYALKYLCARBOXYLIC ACID DERIVATIVES AND PROCESS FOR THEIR PREPARATIONS

(75) Inventors: Mitsuo Ohashi, Saitama-ken (JP); Katsuya Awano, Tochigi-ken (JP); Toshio Tanaka, Tochigi-ken (JP); Tetsuya Kimura, Tochigi-ken (JP)

(73) Assignee: Kyorin Pharmaceutical Co., Ltd., Tokyo (JP)

(21) Appl. No.: 10/622,589

(22) Filed: Jul. 21, 2003

Related U.S. Patent Documents

Reissue of:
(64) Patent No.: 4,985,585
Issued: Jan. 15, 1991
Appl. No.: 07/313,900
Filed: Feb. 23, 1989

(30) Foreign Application Priority Data

Mar. 7, 1988 (JP) ..... 63-53374

(51) Int. Cl.[7] ..... C07C 32/00
(52) U.S. Cl. ..... 560/9; 560/11; 562/426; 562/429
(58) Field of Search ..... 560/9, 11; 562/426, 562/429

(56) References Cited

U.S. PATENT DOCUMENTS 4,507,498 A * 3/1985 Carson et al. ..... 562/463
4,985,585 A 1/1991 Ohashi et al.
5,023,364 A 6/1991 Ohashi et al.
5,290,812 A 3/1994 Ohashi et al.

FOREIGN PATENT DOCUMENTS

EP 56172 A * 7/1982 ..... A61K/31/19
GB 2058785 A * 4/1981 ..... C07C/59/90

OTHER PUBLICATIONS

Burger, "Medicinal Chemistry," 2nd Ed., pp. 72–88 (1960).*

* cited by examiner

*Primary Examiner*—Michael L. Shippen
(74) *Attorney, Agent, or Firm*—Oblon, Spivak, McClelland, Maier & Neustadt, P.C.

(57) ABSTRACT

Phenoxyalkylcarboxylic acid derivative represented by the following formula, (I)

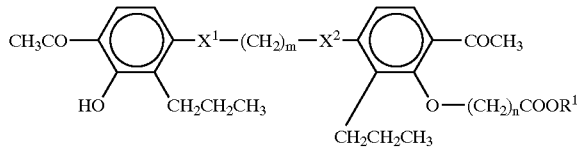

wherein $R^1$ indicates hydrogen atom, methyl group or ethyl group, m is an integer from 2 to 5, and n is an integer from 3 to 8, $X^1$ and $X^2$ each independently represent sulfur atom, oxygen atom, sulfinyl group or sulfonyl group, proviso $X^1$ and $X^2$ are not simultaneously oxygen atom; their alkali salts and hydrates thereof are useful as antiallergic agents.

2 Claims, No Drawings

PHENOXYALKYLCARBOXYLIC ACID DERIVATIVES AND PROCESS FOR THEIR PREPARATIONS

Matter enclosed in heavy brackets [ ] appears in the original patent but forms no part of this reissue specification; matter printed in italics indicates the additions made by reissue.

BACKGROUND OF THE INVENTION

1. Field of the Invention

This invention is concerned with certain novel phenoxyalkylcarboxylic acid derivatives which have strong and selective leukotriene antagonist activity, and are useful for prevention and treatment of allergic diseases such as bronchial asthma and so on, their intermediates and their preparation processes thereof.

Moreover, it relates to certain novel phenoxyalkylcarboxylic acid derivatives of the general formula (I), (I)

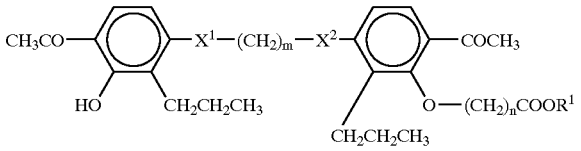

wherein $R^1$ indicates hydrogen atom, methyl group or ethyl group, m is an integer from 2 to 5, and n is an integer from 3 to 8, $X^1$ and $X^2$ each independently represents sulfur atom, oxygen atom, sulfinyl group or sulfonyl group, proviso $X^1$ and $X^2$ are not simultaneously oxygen atom; their alkali salts and hydrates thereof.

2. Description of the Prior Art

Leukotrienes (leukotriene $C_4$, $D_4$, $E_4$), which are metabolites of arachidonic acid through 5'-lipoxygenase pathway, are constituents of SRS-A (slow reacting substance of anaphylaxis), being an important mediator of the immediate type allergic diseases such as bronchial asthma. Accordingly, the drugs which exert antagonistic effects on leukotrienes are promising in the treatment of allergic diseases. But, only few drugs having those effects through the internal use are known and none is practically used.

Compounds having somewhat similar structure with those of the present invention are described in Japanese Patent Unexamined Publication (Kokai) Sho No. 58-189137 which corresponds to U.S. Pat. No. 4,507,498. These compounds can be characterized by the ether bond, but they never have thioether bond and thus, they are structurally different from the compounds of the present invention. Moreover, the compounds described in the art have been revealed to be less effective and are not useful as compared with the compounds of the present invention.

3. Detailed Description of the Invention

As the result of diligent studies about leukotriene antagonists, the inventors have found that the compounds represented by the general formula (I) possess strong and selective leukotriene antagonist activity even afier an oral administration and further found that they have surprisingly therapeutic effects on airway hyperreactivity induced in guinea pigs, which lead to completion of the present invention.

According to the present invention, the compounds of the general formula (I) can be prepared on the hereinafter mentioned routes. (1) Compound of the general formula (Ia)

can be prepared by allowing compounds of the general formula (II) to react with compounds of the general formula (III)

(Ia)

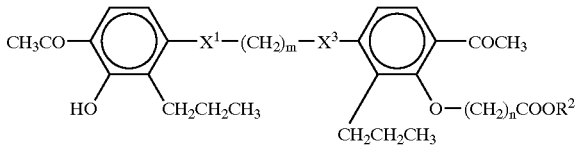

(wherein $R^2$ indicates methyl group or ethyl group, m is an integer from 2 to 5, n is an integer from 3 to 8, $X^1$ indicates sulfur atom, oxygen atom, sulfinyl group or sulfonyl group, $X^3$ indicates sulfur atom or oxygen atom, proviso $X^1$ and $X^3$ are not simultaneously oxygen atom)

(II)

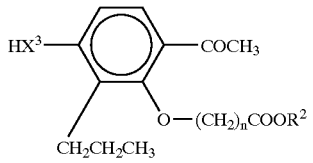

(wherein $R^2$, n and $X^3$ are as defined in the above)

(III)

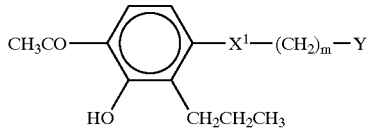

(wherein Y indicates, halogen atom and $X^1$ are as defined in the above)

It is preferable that this reaction is conducted in an organic solvent, for example acetone, methylethylketone, diethylketone or dimethylformamide etc. under a reaction temperature of the room temperature to the solvent refluxing temperature. In addition, the presence of an inorganic base, for example potassium carbonate or sodium carbonate etc. and further the addition of potassium iodide are also recommendable.

(2) Compounds represented by the general formula (Ib) can be prepared by allowing compounds of the general formula (IV) to react with compounds of formula (V).

(Ib)

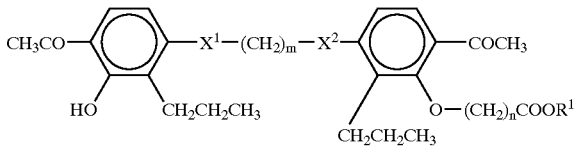

(wherein $R^2$ indicates methyl group or ethyl group, m is an integer from 2 to 5, n is an integer from 3 to 8, $X^2$ indicates sulfur atom, oxygen atom, sulfinyl group or sulfonyl group and $X^3$ indicates sulfur atom or oxygen atom, proviso $X^2$ and $X^3$ are not simultaneously oxygen atom)

(IV)

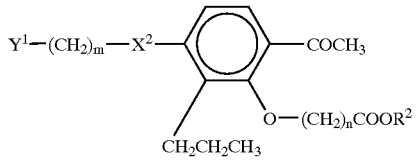

(wherein $Y^1$ indicates halogen atom, and $R^2$, $X^2$, m and n are as defined in the above)

(V)

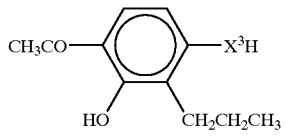

(wherein $X^3$ is as defined in the above)

It is preferable that this reaction is conducted in an organic solvent, for example acetone, methylethylketone, diethylketone or dimethylformamide etc. under a reaction temperature of the room temperature to the solvent refluxing temperature. In addition, the presence of an inorganic base, for example potassium carbonate or sodium carbonate etc. and further the addition of potassium iodide are also recommendable.

(3) Compounds represented by the general formula (IIa) can be prepared by allowing compounds of the general formula (VI) to react with compounds of the general formula (VII), followed by removing the protective group.

(IIa)

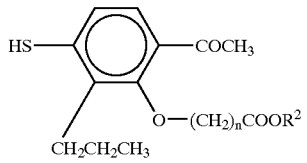

(wherein $R^2$ indicates methyl group or ethyl group and n is an integer from 3 to 8)

(VI)

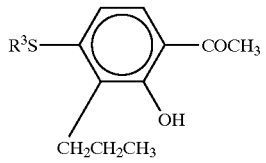

(wherein $R^3$ indicates a protective group)

$$Y^2\text{-}(CH_2)_nCOOR^2 \quad \text{(VII)}$$

(wherein $Y^2$ indicates halogen atom, and $R^2$ and n are as defined in the above)

It is preferable that this reaction is conducted in an organic solvent, for example acetone, methylethylketone, diethylketone or dimethylformamide etc. under a reaction temperature of the room temperature to the solvent refluxing temperature. In addition, the presence of an inorganic base, for example potassium carbonate or sodium carbonate and further the addition of potassium iodide are also recommendable.

In the compounds of the general formula (VI), dimethylaminocarbonyl group or benzyl group etc. can be exemplified as the protective group for thiol group.

(4) The compounds represented by the general formula (IIa) can also be prepared by the following process. The compounds of the general formula (VI) are allowed to react with compounds of the general formula (VIIIa) to give compounds of the general formula (IX).

$$Y\text{—}(CH_2)_n\text{—}Y^1 \quad \text{(VIIIa)}$$

(wherein Y and $Y^1$ indicate identical or different halogen atom, and n is an integer from 3 to 8)

(IX)

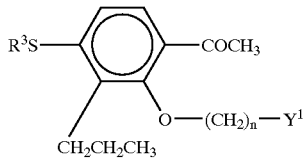

(wherein $R^3$ indicates a protective group, $Y^1$ and n are as defined in the above)

It is preferable that this reaction is conducted in an organic solvent, for example acetone, methylethylketone, diethylketone or dimethylformamide under a reaction temperature of the room temperature to the solvent refluxing temperature. Then, the compounds represented by the general formula (IX) are allowed to react with sodium cyanide or potassium cyanide to give compounds of the general formula (X).

(X)

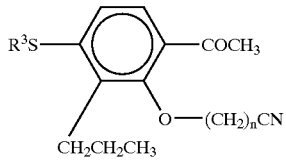

(wherein $R^3$ and n are as defined in the above)

It is preferable that this reaction is conducted in an organic solvent, for example dimethyl sulfoxide or dimethylformamide under a temperature of the room temperature to 100° C. Further, the compounds represented by the general formula (X) are subjected to hydrolysis and then to esterification with alcohol to give the compounds of the general formula (IIa). The hydrolysis of nitrile proceeds preferably with sodium hydroxide or potassium hydroxide in aqueous solution, and the esterification is preferably performed by refluxing in alcohol and in the presence of conc. sulfuric acid or a certain amount of a catalyst.

(5) Compounds represented by the general formula (IVa) can be prepared by allowing the compounds of the general formula (IIa) to react with compounds of the general formula (VIII).

(IVa)

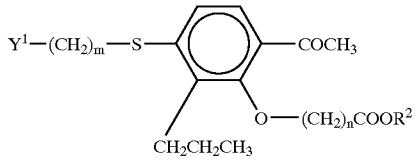

(wherein $R^2$ indicates methyl group or ethyl group, $Y^1$ indicates a halogen atom, m is an integer from 2 to 5 and n is an integer from 3 to 8)

$$Y—(CH_2)_m—Y^1 \quad \text{(VIII)}$$

(wherein Y indicates a halogen atom, $Y^1$ and m are as defined in the above)

It is preferable that this reaction is conducted in an organic solvent, for example acetone, methylethylketone, diethylketone or dimethylformamide under a reaction temperature of the room temperature to the solvent refluxing temperature. In addition, the presence of an inorganic base, for example potassium carbonate or sodium carbonate and further the addition of potassium iodide are also preferable.

(6) Compounds of the general formula (III) or (IV), in which $X^1$ and $X^2$ are both sulfinyl group, can be prepared by oxidizing compounds represented by the general formula (IIIa) or (IVa).

(IIIa)

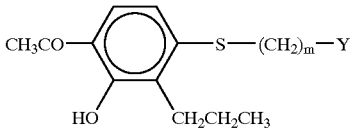

(wherein Y indicates a halogen atom and m is an integer from 2 to 5)

(IVa)

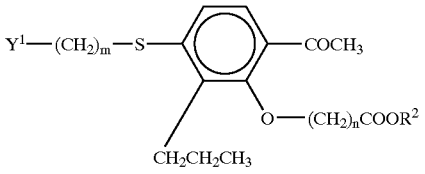

(wherein $Y^1$ indicates a halogen atom, $R^2$ indicates methyl group or ethyl group, m is an integer from 2 to 5 and n is an integer from 3 to 8)

The compounds of the general formula (III) or (IV) can typically be prepared by allowing the compounds represented by the general formula (IIIa) or (IVa) to react with a mild oxidizing agent, for example m-chloroperbenzoic acid, hydrogen peroxide etc., of equimolar or excess amount in an adequate solvent, for example methylene chloride, alcohol etc. respectively.

(7) Compounds of the general formula (III) or (IV), in which $X^1$ and $X^2$ are both sulfonyl group, can be prepared by allowing the compounds of the general formula (IIIa), (IVa) to react likewise as in (6), but with not less than bimolar amount of the mild oxidizing agent.

(8) Compounds of the general formula (I), in which $R^1$ is methyl group or ethyl group $X^1$ is oxygen atom or sulfonyl group and $X^2$ is sulfinyl group, and compounds of the general formula (I), in which $R^1$ is methyl group or ethyl group, $X^1$ is sulfinyl group and $X^2$ is an oxygen atom or sulfonyl group, can be respectively prepared by allowing the compounds represented by the general formula (Ia'), (Ib') to react with equimolar or excess amount of the mild oxidizing agent likewise as in (6).

(Ia')

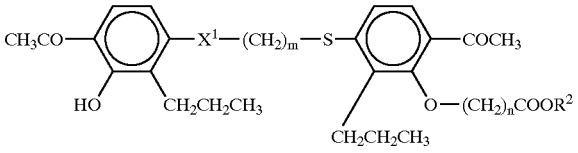

(wherein $R^2$ indicates methyl group or ethyl group, m is an integer from 2 to 5, n is an integer from 3 to 8, and $X^1$ indicates oxygen atom or sulfonyl group)

(Ib')

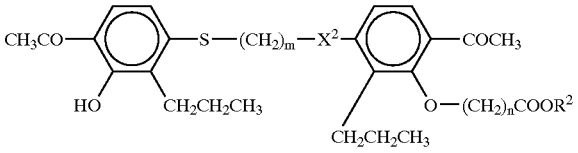

(wherein $R^2$, m, n and $X^2$ are defined in the above)

(9) Compounds of the general formula (I), in which $R^1$ is methyl group or ethyl group, $X^1$ oxygen atom or sulfonyl group and $X^2$ is sulfonyl group, and compounds of the general formula (I), in which $R^1$ is methyl group or ethyl group, $X^1$ is sulfonyl group and $X^2$ is oxygen atom or sulfonyl group can be respectively prepared by allowing the compounds represented by the general formula (Ia'), (Ib') to react with the mild oxidizing agent likewise as in (6) but with not less than bimolar amount.

EXAMPLES

The present invention is hereinafter explained by concrete examples, but the present invention can no to be restricted by these examples.

EXAMPLE 1

Ethyl 4-[6-acetyl-3-[3-(4-acetyl-3-hydroxy-2-propylphenylthio)propoxy]-2-propylphenoxy]butyrate To a stirring mixture of ethyl 4-(6-acetyl-3-hydroxy-2-propylphenoxy)butyrate (1.6 g), potassium iodide (0.5 g) and potassium carbonate (1.45 g) in acetone (30 ml) was added a solution of [4-(3-bromopropylthio)-2-hydroxy-3-propylphenyl]ethanone (1.9 g) in acetone (10 ml) dropwise with heating to reflux. After heating and refluxing with stirring for six hours, inorganic materials were separated by filtration and the filtrate was concentrated. The residue was separated and purified through silica-gel column chromatography (eluting with benzene:ethyl acetate=9:1) to give the title compound as crude crystals (2.1 g, 72.4%). This crystal was recrystallized from ethanol to colorless crystals, mp 65–66° C.

Analysis (%) for $C_{31}H_{42}O_7S$, Calcd. (Found): C, 66.64 (66.53); H, 7.58 (7.72).

EXAMPLE 2–7

Likewise as in Example 1, compounds listed in Table 1 were synthesized.

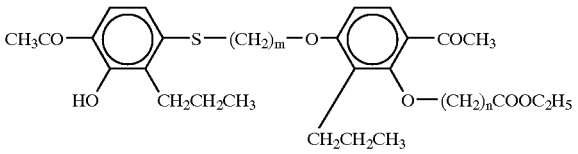

TABLE 1

| Example | m | n | Yield (%) | Analysis (%) | Calcd./Found |
|---|---|---|---|---|---|
| 2 | 3 | 4 | 70.4 | C: 67.10 | H: 7.74 |
| | | | | 67.24 | 7.88 |
| 3 | 3 | 5 | 75.0 | C: 67.55 | H: 7.90 |
| | | | | 67.54 | 7.91 |
| 4 | 3 | 6 | 58.3 | C: 67.97 | H: 8.05 |
| | | | | 68.03 | 8.10 |
| 5 | 3 | 8 | 66.9 | C: 68.76 | H: 8.33 |
| | | | | 68.79 | 8.33 |
| 6 | 4 | 3 | 63.9 | C: 67.10 | H: 7.74 |
| | | | | 67.08 | 7.89 |
| 7 | 5 | 3 | 65.7 | C: 67.55 | H: 7.90 |
| | | | | 67.49 | 7.93 |

EXAMPLE 8

Ethyl 4-[6-acetyl-3-[2-(4-acetyl-3-hydroxy-2-propylphenylthio)ethoxy]-2-propylphenoxy]butyrate A mixture of ethyl 4-[6-acetyl-3-(2-chloroethoxy)-2-propylphenoxy]butyrate (0.60 g), (2-hydroxy-4-mercapto-3-propylphenyl)ethanone (0.51 g), potassium iodide (0.1 g) and potassium carbonate (0.65 g) in acetone (40 ml) was heated and refluxed with stirring for 19 hours. After cooled, inorganic materials were separated by filtration and the filtrate was concentrated. The resultant residue was separated and purified through silica gel column chromatography (eluting with benzene:ethyl acetate=15:1, then 9:1) to give the title compound (0.73 g, 82.8%) as brown oil.

Analysis (%) for $C_{30}H_{40}O_7S$, Calcd. (Found): C, 66.15 (66.12); H, 7.40 (7.50).

EXAMPLE 9,10

Likewise as in Example 8, the compounds listed in Table 2 were synthesized.

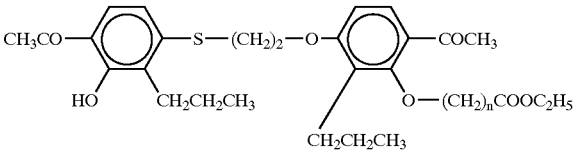

TABLE 2

| Example | n | Yield (%) | Analysis (%) | Calcd./Found |
|---|---|---|---|---|
| 9 | 4 | 76.5 | C: 66.64 | H: 7.58 |
| | | | 66.64 | 7.59 |
| 10 | 5 | 64.7 | C: 67.10 | H: 7.74 |
| | | | 67.14 | 7.74 |

EXAMPLE 11

Ethyl 4-(6-acetyl-3-mercapto-2-propylphenoxy)butyrate (1) A mixture of (4-(N,N-dimethylcarbamoylthio)-2-hydroxy-3-propylphenyl)ethanone (26.6 g), ethyl 4-bromobutyrate (92.9 g), potassium iodide (1 g) and potassium carbonate (26.1 g) in acetone (200 ml) was heated and refluxed with stirring. Each of potassium carbonate (13 g) was added thereto after 9 hours and 14 hours, and the mixture was heated and refluxed with stirring for total 29 hours. Then, inorganic materials were separated and the solution was concentrated under a reduced pressure. The resultant residue was purified through silica-gel column chromatography (eluting with hexane, then benzene and finally benzene:ethyl acetate=9:1) to give ethyl 4-(6-acetyl-3-(N,N-dimethylcarbamoylthio) -2-propylphenoxy)butyrate (31.5 g, 84.2%) as light brown crystal, mp 60–63° C.

Analysis (%) for $C_{20}H_{29}NO_5S$, Calcd. (Found): C, 60.74 (60.89); H, 7.39 (7.58); N, 3.54 (3.38).

(2) Ethyl 4-(6-acetyl-3-(N,N-dimethylcarbamoylthio)-2-propylphenoxy)butyrate (10.6 g) and potassium hydroxide (4.5 g) in ethanol (100 ml) were heated with stirring under refluxing for 1.5 hours. Ice water and conc. sulfuric acid were added thereto (pH 1), and then the mixture was subjected to extraction. The organic layer was washed with water and aqueous solution of sodium chloride, followed by being dried over sodium sulfate and then concentrated under a reduced pressure. To the resultant residue was added a mixture of ethanol (30 ml) and conc. sulfuric acid (0.5 ml), and the mixture was heated with stirring and refluxing for 1.5 hours. Ice water was added thereto and the mixture was extracted with ethyl acetate. The organic layer was washed with water and thereafter was dried over sodium sulfate, followed by being concentrated under a reduced pressure. Ethyl 4-(6-acetyl-3-mercapto-2-propylphenoxy)butyrate (7.8 g, 89.7%) was obtained as brown oil.

$^1$H—NMR ($CDCl_3$) δ:1.03 (3H, t, J=7 Hz, —$CH_2CH_2CH_3$), 1.28 (3H, t, J=7 Hz, $CO_2CH_2CH_3$), 1.57 (2H, m, —$CH_2CH_2CH_3$), 2.12 (2H, m, —$OCH_2CH_2CH_2COOEt$), 2.5 (2H, m, —$CH_2CO_2Et$), 2.57 (3H, s, $COCH_3$), 2.6 (2H, m, —$CH_2CH_2CH_3$), 3.78 (2H, t, J=6 Hz, —$OCH_2CH_2CH_2CO_2Et$), 4.16 (2H, q, J=7 Hz, $CO_2CH_2CH_3$), 7.10 (1H, d, J=8 Hz,

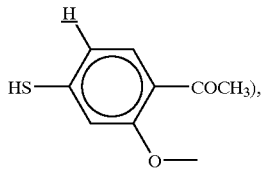

7.28 (1H, d, J=8 Hz),

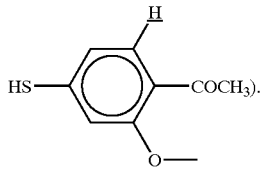

EXAMPLE 12

Ethyl 5-(6-acetyl-3-mercapto-2-propylphenoxy) pentanate

Likewise as in Example 11, the title compound was quantitatively obtained as brown oil. $^1$H—NMR ($CDCl_3$) δ:

1.03 (3H, t, J=7 Hz, —$CH_2CH_2CH_3$), 1.27 (3H, t, J=7 Hz, 2.39 (2H, m, —$CH_2CO_2Et$), 2.57 (3H, s, $COCH_3$), 2.70 (2H, m, —$CH_2CH_2CH_3$), 3.75 (2H, m, —$OCH_2(CH_2)_3CO_2Et$), 4.14 (2H, q, J=7 Hz, $CO_2CH_2CH_3$), 7.10 (1H, d, J=8 Hz,

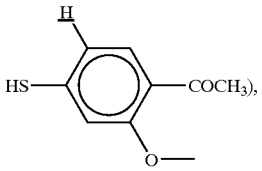

7.28 (1H, d, J=8 Hz),

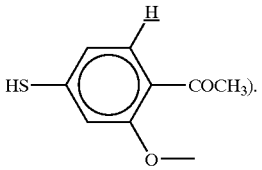

EXAMPLE 13

Ethyl 6-(6-acetyl-3-mercapto-2-propylphenoxy)hexanate

Likewise as in Example 11, the title compound was obtained as brown oil with yield of 69.0%.

$^1$H—NMR ($CDCl_3$) δ: 1.02 (3H, t, J=7 Hz, —$CH_2CH_2CH_3$), 1.26 (3H, t, J=7 Hz, $CO_2CH_2CH_3$), 1.66 (8H, m, —$OCH_2CH_2CH_2CH_2CH_2CO_2Et$ and —$CH_2CH_2CH_3$), 2.34 (2H, t. J=7 Hz, —$CH_2CO_2Et$), 2.57 (3H, s, $COCH_3$), 2.60 (2H, m, —$CH_2CH_2CH_3$), 3.73 (2H, t, J=6 Hz, —$OCH_2(CH_2)_4CO_2Et$), 4.13 (2H, q, J=7 Hz, —$CO_2CH_2CH_3$), 7.10 (1H, d, J=8 Hz,

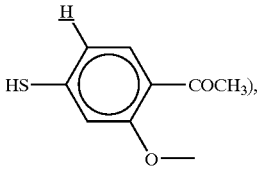

7.28 (1H, d, J=8 Hz),

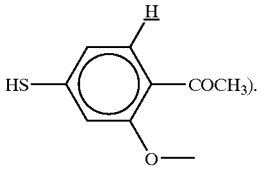

EXAMPLE 14

Ethyl 7-(6-acetyl-3-mercapto-2-propylphenoxy) heptanate (1) A mixture of (4-(N,N-dimethylcarbamoylthio)-2-hydroxy-3 -propylphenoxy)ethanone (5.8 g), 1,6-dibromohexane (25 g), potassium iodide (1 g) and potassium carbonate (5.7 g) in acetone (40 ml) was heated with refluxing and stirring. Each of potassium carbonate (2.9 g) was added thereto after 9.5 hours, 20 hours and 30.5 hours, and the mixture was subjected to refluxing for total 41 hours. After cooled, inorganic materials were filtered off and the filtrate was concentrated under a reduced pressure. The resultant residue was purified through silica-gel column chromatography (eluting with benzene:hexane=1:1, then benzene:ethyl acetate=9: 1) to give (2-(6-bromohexyloxy)-4-(N,N-dimethylcarbamoylthio) -3-propylphenyl)ethanone (7.3 g, 79.7%) as brown oil. $^1$H-NMR ($CDCl_3$) δ: 0.99 (3H, t, J=7 Hz, —$CH_2CH_2CH_3$), 1.2–1.8 (10H, m, —$CH_2CH_2CH_3$ and —$OCH_2CH_2CH_2CH_2CH_2CH_2Br$), 2.59 (3H, s, $COCH_3$), 2.70 (2H, m, —$CH_2CH_2CH_3$), 3.08 (6H, s, —$N(CH_3)_2$), 3.35 (2H, t, J=6 Hz, —$CH_2Br$), 3.77 (2H, m, t, J=6 Hz, —$OCH_2(CH_2)_5Br$), 7.30 (2H,

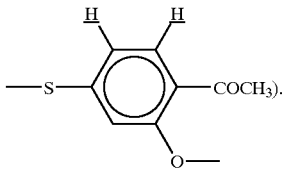

(2) To a mixture of sodium cyanide (0.89 g) in dimethyl sulfoxide (20 ml) heated at a temperature about 50° C. with stirring was added a solution of (2-(6-bromohexyloxy)-4-(N,N-dimethylcarbamoylthio) -3-propylphenyl)ethanone (7.3 g) in dimethyl sulfoxide (40 ml) at 50 to 60° C. After further allowing the reaction for 15 minutes at 90° C., the reaction mixture was poured into icewater and subjected to extraction with ethyl acetate. The organic layer was washed with water, dried over sodium sulfate and concentrated under a reduced pressure. The resultant residue was purified through silica-gel column chromatography (eluting with benzene:ethyl acetate=9:1, then 7:3) to give 7-(6-acetyl-3-(N,N-dimethylcarbamoylthio)-2-propylpheoxy) heptanenitrile (4.4 g, 68.6%) as brown oil. $^1$H—NMR ($CDCl_3$) δ: 0.99 (3H, t, J=7 Hz, —$CH_2CH_2CH_3$), 1.3–2.0 (10H, m, —$CH_2CH_2CH_3$ and —$OCH_2CH_2CH_2CH_2CH_2CH_2CN$), 2.36 (2H, m, —$O(CH_2)_5CH_2CN$), 2.59 (3H, s, $COCH_3$), about 2.8 (2H, m, —$CH_2CH_2CH_3$), 3.08 (6H, s, —$N(CH_3)_2$), 3.77 (2H, t, J=6 Hz, —$OCH_2(CH_2)_5CN$), 7.32 (2H, m,

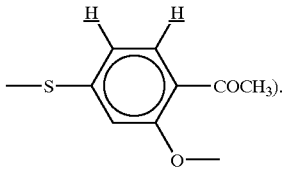

(3) A mixture of 7-(6-acetyl-3-(N,N-dimethylcarbamoylthio)-2-propylphenoxy)heptanenitrile (4.4 g) and potassium hydroxide (1.9 g) in ethanol (30 ml) was heated with refluxing and stirring for 1.5 hours, followed by being concentrated under reduced pressure. To the resultant residue was added ice-water and then conc. hydrochloric acid to be acidic, and the mixture was subjected to extraction with ethyl acetate. The organic layer was washed with water, then dried over sodium sulfate and concentrated under a reduced pressure to give the brown oil (3.7 g). Said brown oil (2.0 g) and potassium hydroxide (2.0 g) in water (20 ml) was heated with refluxing and stirring for three hours, followed by being concentrated under reduced pressure. To the resultant residue was added ice-water and then conc. hydrochloric acid to be acidic, and the mixture was subjected to extraction with ethyl acetate. The organic layer was washed with water, then dried over magnesium sulfate and concentrated under a reduced pressure. To the resultant residue was added a mixture of conc. sulfuric acid (0.5 ml) and ethanol (20 ml), and the mixture was further subjected to refluxing for 1.5 hours. To the mixture was added ice-water, and the mixture was extracted with ethyl acetate. The organic layer was washed with water and aqueous solution of sodium chloride, dried over sodium sulfate and concentrated under reduced pressure. 1.8 g of ethyl 7-(6-acetyl-3-mercapto-2-propylphenoxy)heptanate (78.4%) was obtained as brown oil. $^1$H—NMR ($CDCl_3$) δ: 1.02 (3H, t, J=7 Hz, —$CH_2CH_2CH_3$), 1.26 (3H, t, J=7 Hz, —$CO_2CH_2CH_3$), 1.2–2.0 (10H, m, —$OCH_2CH_2CH_2CH_2CH_2CH_2CO_2Et$ and —$CH_2CH_2CH_3$), 2.31 (2H, m, —$CH_2CO_2Et$), 2.57 (3H, s, $COCH_3$), about 2.6 (2H, m, —$CH_2CH_2CH_3$), 3.72 (2H, t, J=6 Hz, —$OCH_2(CH_2)_5CO_2Et$), 4.12 (2H, q, J=7 Hz, $CO_2CH_2H_3$), 7.01 (1H, d, J=8 Hz,

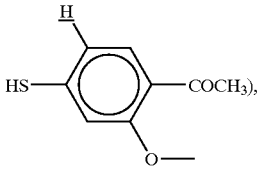

7.27 (1H, d, J=8 Hz),

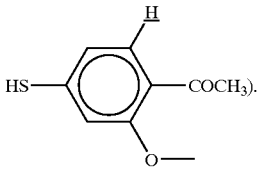

EXAMPLE 15

Ethyl 9-(6-acetyl-3 -mercapto-2-propylphenoxy)nonanate

Likewise as in Example 14, the title compound was obtained as brown oil with overall yield of 67.3%. $^1$H—NMR ($CDCl_3$) δ: 1.03 (3H, t, J=7 Hz, —$CH_2CH_2CH_3$), 1.26 (3H, t, J=7 Hz, —$CO_2CH_2CH_3$), 1.2–2.0 (14H, m, —$CH_2CH_2CH_3$ and —$OCH_2CH_2CH_2CH_2CH_2CH_2CH_2CH_2CO_2Et$) 2.30 (2H, t, J=7 Hz, —$CH_2CO_2Et$), 2.58 (3H, s, $COCH_3$), about 2.6 (2H, m—$CH_2CH_2CH_3$), 3.72 (2H, t, J=6 Hz, —$OCH_2(CH_2)_7CO_2Et$), 4.12 (2H, q, J=7 Hz, —$CO_2CH_2CH_3$), 7.01 (1H, d, J=8 Hz,

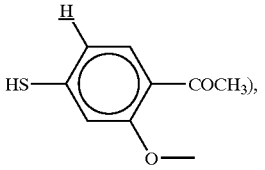

7.28 (1H, d, J=8 Hz),

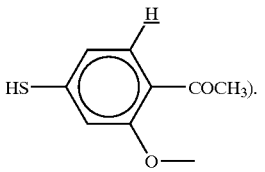

EXAMPLE 16

Ethyl 4-[6-acetyl-3-[3-(4-acetyl-3-hydroxy-2-propylphenylthio)-propylthio]-2-propylphenoxy]butyrate.

A mixture of ethyl 4-(6-acetyl-3-mercapto-2-propylphenoxy)butyrate (2.0 g), (4-(3-bromopropylthio)-2-hydroxy-3-propylphenyl)ethanone (2.0 g), potassium iodide (0.5 g) and potassium carbonate (1.7 g) in acetone (40 ml) was heated with refluxing and stirring for 9 hours. After cooled, inorganic materials were separated by filtration and the filtrate was concentrated. The resultant residue was separated, and was purified through silicagel column chromatography (eluting with benzene:ethyl acetate=9:1) to give the title compound (1.8 g, 50.8%) as yellow oil.

Analysis (%) for $C_{31}H_{42}O_6S_2$, Calcd. (Found): C, 64.78 (64.66); H, 7.36 (7.38).

EXAMPLE 17–22

Likewise as in Example 16, the compounds listed in Table 3 were synthesized.

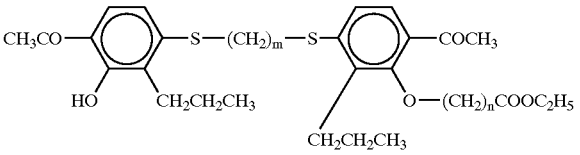

TABLE 3

| Example | m | n | Yield (%) | Analysis (%) | Calcd./Found |
|---|---|---|---|---|---|
| 17 | 3 | 4 | 77.8 | C: 65.27<br>65.33 | H: 7.53<br>7.59 |
| 18 | 3 | 5 | 84.1 | C: 65.75<br>65.78 | H: 7.69<br>7.69 |
| 19 | 3 | 6 | 59.4 | C: 66.20<br>66.22 | H: 7.84<br>7.88 |
| 20 | 3 | 8 | 61.2 | C: 67.04<br>67.15 | H: 8.13<br>8.14 |
| 21 | 4 | 3 | 77.8 | C: 65.27<br>65.23 | H: 7.53<br>7.49 |
| 22 | 5 | 3 | 80.7 | C: 65.75<br>65.87 | H: 7.69<br>7.70 |

EXAMPLE 23

Ethyl 4-[6-acetyl-3-[3-(4-acetyl-3-hydroxy-2-propylphenoxy)propylthio]-2-propyl phenoxy]butyrate A mixture of ethyl 4-(6-acetyl-3-mercapto-2-propylphenoxy)-butyrate (1.7 g), (4-(3-bromopropoxy)-2-hydroxy-3-propylphenyl)ethanone (1.7 g), potassium iodide (0.5 g) and potassium carbonate (1.45 g) in acetone (40 ml) was heated with refluxing and stirring for 7.5 hours. Ice-water and conc. hydrochloric acid were added thereto, and the mixture was subjected to extraction with ethyl acetate. After washed with water, the extract was dried over sodium sulfate and concentrated under a reduced pressure. The resultant residue was separated and purified through silicagel column chromatography (eluting with benzene:ethyl acetate=9:1) to give the title compound (2.08 g, 71.0%) as light yellow crystal, mp 87–88° C.

Analysis (%) for $C_{31}H_{42}O_7S$, Calcd. (Found): C, 66.64 (66.85); H, 7.58 (7.56).

EXAMPLE 24–30

Likewise as in Example 23, the compounds listed in Table 4 were synthesized.

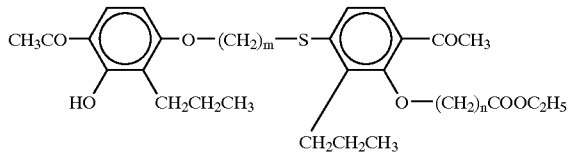

TABLE 4

| Example | m | n | Yield (%) | mp (° C.) | Analysis (%) | Calcd./Found |
|---|---|---|---|---|---|---|
| 24 | 2 | 3 | 77.4 | oil | C: 66.15<br>65.87 | H: 7.40<br>7.39 |
| 25 | 3 | 4 | 83.4 | oil | C: 67.10<br>67.20 | H: 7.74<br>7.79 |
| 26 | 3 | 5 | 78.8 | oil | C: 67.55<br>67.56 | H: 7.90<br>7.87 |
| 27 | 3 | 6 | 68.6 | oil | C: 67.97<br>67.97 | H: 8.05<br>8.11 |
| 28 | 3 | 8 | 50.2 | oil | C: 68.76<br>68.84 | H: 8.33<br>8.36 |
| 29 | 4 | 3 | 74.3 | oil | C: 67.10<br>67.04 | H: 7.74<br>7.76 |
| 30 | 5 | 3 | 82.9 | oil | C: 67.55<br>67.62 | H: 7.90<br>7.88 |

EXAMPLE 31

Ethyl 4-[6-acetyl -3-[3-(4-acetyl-3-hydroxy-2-propylphenylsulfinyl)propoxy]-2-propylphenoxy]butyrate To a mixture of ethyl 4-[6-acetyl-3-[3-(4-acetyl-3-hydroxy-2-propylphenylthio)propoxy]-2-propylp henoxy] butyrate (1.2 g) in methylene chloride (40 ml) was added m-chloroperbenzoic acid (0.51 g) on ice-water bath and was subjected to stirring at the same temperature for 2 hours. The obtained organic layer was washed twice with a cooled aqueous solution of potassium carbonate, then with a saturated aqueous solution of sodium chloride, dried over sodium sulfate and concentrated. The resultant residue was purified through silica-gel column chromatography (eluting with benzene:ethyl acetate=1:1) to give the title compound (0.78 g, 63.2%) as colorless crystal, mp 74–76° C.

Analysis (%) for $C_{31}H_{42}O_8S$, Calcd. (Found): C, 64.78 (64.78); H, 7.37 (7.43).

EXAMPLE 32

Ethyl 4-[6-acetyl-3-[3-(4-acetyl-3-hydroxy-2-propylphenylsulfonyl)propoxy]-2-propylphenoxy]butyrate To a mixture of ethyl 4-[6-acetyl-3-[3-(4-acetyl-3-hydroxy-2-propylphenylthio)propoxy]-2-propylp henoxy] butyrate (1.3 g) in methylene chloride (40 ml) was added m-chloroperbenzoic acid (1.05 g) on ice-water bath and was subjected to stirring at the same temperature for one hour, followed further by stirring at a room temperature for 3 hours. The obtained organic layer was washed twice with cooled aqueous solution of potassium carbonate, then with saturated aqueous solution of sodium chloride, dried over sodium sulfate and concentrated. The resultant residue was purified through silica-gel column chromatography (eluting with benzene:ethyl acetate=9:1, then 7:3) to give the title compound (0.97 g, 70.6%) as colorless crystal, mp 77–79° C.

Analysis (%) for $C_{31}H_{42}O_9S$, Calcd. (Found): C, 63.03 (63.11); H, 7.17 (7.19).

EXAMPLE 33

4-[6-Acetyl-3-[3-(4-acetyl-3-hydroxy-2-propylphenylthio)propoxy]-2-propylphenoxy]butyric acid To a mixture of ethyl 4-[6-acetyl-3-[3-(4-acetyl-3-hydroxy-2-propylphenylthio)propoxy]-2-propylphenoxy] butyrate (2.1 g) in ethanol (10 ml) was added a solution of sodium hydroxide (0.26 g) dissolved into water (10 ml). After heated on hot water bath for 5 minutes, the mixture was cooled by adding ice-water and was made acidic by addition of hydrochloric acid, followed by being extracted with ethyl acetate. The obtained layer was washed with water, dried over sodium sulfate and concentrated. The resultant residue was separated and purified through silica-gel column chromatography (eluting with ethanol:methylene chloride=3:100) to give the title compound (1.3 g, 65.2%) as colorless crystal, mp 79–81° C.

Analysis (%) for $C_{29}H_{38}O_7S$, Calcd. (Found): C, 65.64 (65.81), H, 7.22 (7.24).

EXAMPLE 34–64

Likewise as in Example 33, the compounds listed in Table 5 were synthesized.

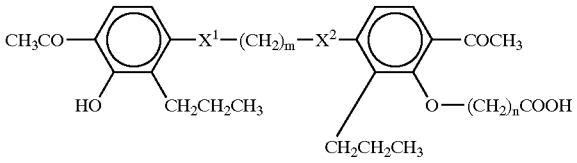

TABLE 5

| Ex. | $X^1$ | $X^2$ | m | n | Yield (%) | mp (° C.) | Analysis (%) | Calcd./Found |
|---|---|---|---|---|---|---|---|---|
| 34 | S | O | 3 | 4 | 74.3 | oil | C: 66.15<br>66.18 | H: 7.40<br>7.46 |
| 35 | S | O | 3 | 5 | 84.6 | oil | C: 66.64<br>66.47 | H: 7.58<br>7.64 |
| 36 | S | O | 3 | 6 | 96.7 | oil | C: 67.10<br>67.25 | H: 7.74<br>7.79 |
| 37 | S | O | 3 | 8 | 94.2 | oil | C: 67.97<br>68.13 | H: 8.05<br>8.09 |
| 38 | S | O | 4 | 3 | 55.3 | oil | C: 66.15<br>66.19 | H: 7.40<br>7.57 |
| 39 | S | O | 5 | 3 | 78.7 | oil | C: 66.64<br>66.61 | H: 7.58<br>7.56 |
| 40 | S | O | 2 | 3 | 76.5 | oil | C: 65.09<br>64.85 | H: 7.02<br>7.05 |
| 41 | S | O | 2 | 4 | 64.8 | oil | C: 65.64<br>65.45 | H: 7.22<br>7.29 |
| 42 | S | O | 2 | 5 | 89.0 | oil | C: 66.15<br>65.92 | H: 7.40<br>7.39 |
| 43 | SO | O | 3 | 3 | 80.9 | 62–64 | C: 63.72<br>63.58 | H: 7.01<br>7.28 |
| 44 | $SO_2$ | O | 3 | 3 | 81.5 | 109–111 | C: 61.90<br>61.84 | H: 6.81<br>6.83 |
| 45 | S | S | 3 | 3 | 77.1 | 82–84 | C: 63.71<br>63.69 | H: 7.01<br>7.12 |
| 46 | S | S | 3 | 4 | 67.6 | oil | C: 64.26<br>64.11 | H: 7.19<br>7.31 |
| 47 | S | S | 3 | 5 | 88.0 | oil | C: 64.78<br>64.58 | H: 7.36<br>7.51 |
| 48 | S | S | 3 | 6 | 83.8 | oil | C: 65.27<br>65.43 | H: 7.53<br>7.58 |
| 49 | S | S | 3 | 8 | 89.9 | oil | C: 66.20<br>66.36 | H: 7.84<br>7.92 |

TABLE 5-continued

| Ex. | $X^1$ | $X^2$ | m | n | Yield (%) | mp (° C.) | Analysis (%) | Calcd./ Found |
|---|---|---|---|---|---|---|---|---|
| 50 | S | S | 4 | 3 | 85.8 | 62–65 | C: 64.26 | H: 7.19 |
| | | | | | | | 63.99 | 7.31 |
| 51 | S | S | 5 | 3 | 88.1 | oil | C: 64.78 | H: 7.36 |
| | | | | | | | 64.75 | 7.45 |
| 52 | O | S | 2 | 3 | 81.1 | 120–125 | C: 65.09 | H: 7.02 |
| | | | | | | | 65.23 | 6.98 |
| 53 | O | S | 3 | 3 | 68.8 | 70–72 | C: 65.64 | H: 7.22 |
| | | | | | | | 65.71 | 7.23 |
| 54 | O | S | 3 | 4 | 87.2 | oil | C: 66.15 | H: 7.40 |
| | | | | | | | 65.95 | 7.47 |
| 55 | O | S | 3 | 5 | 87.5 | 55–58 | C: 66.64 | H: 7.58 |
| | | | | | | | 66.60 | 7.57 |
| 56 | O | S | 3 | 6 | 69.9 | oil | C: 67.10 | H: 7.74 |
| | | | | | | | 67.07 | 7.75 |
| 57 | O | S | 3 | 8 | 78.5 | oil | C: 67.97 | H: 8.04 |
| | | | | | | | 68.13 | 8.12 |
| 58 | O | S | 4 | 3 | 77.6 | 53–55 | C: 66.15 | H: 7.40 |
| | | | | | | | 65.95 | 7.59 |
| 59 | O | S | 5 | 3 | 84.0 | oil | C: 66.64 | H: 7.58 |
| | | | | | | | 66.51 | 7.74 |
| 60 | O | SO | 3 | 3 | 83.1 | oil | C: 63.72 | H: 7.01 |
| | | | | | | | 63.54 | 7.05 |
| 61 | O | $SO_2$ | 3 | 3 | quant.* | 83–85 | C: 61.90 | H: 6.81 |
| | | | | | | | 61.79 | 6.78 |
| 62 | SO | S | 3 | 3 | 93.0 | oil | C: 61.90 | H: 6.81 |
| | | | | | | | 61.53 | 6.92 |
| 63 | $SO_2$ | S | 3 | 3 | 83.9 | 97–99 | C: 60.18 | H: 6.62 |
| | | | | | | | 60.14 | 6.64 |
| 64 | $SO_2$ | SO | 3 | 3 | 86.6 | oil | C: 58.57 | H: 6.44 |
| | | | | | | | 58.58 | 6.52 |

*quantitatively

EXAMPLE 65

Ethyl 4-[6-acetyl-3-[3-(4-acetyl-3-hydroxy-2-propylphenoxy)propylsulfinyl]-2-propylphenoxy]butyrate Likewise as in Example 31, the title compound was obtained as pale yellow oil with yield of 81.0%.

Analysis (%) for $C_{31}H_{42}O_8S$, Calcd. (Found): C, 64.78 (64.76); H, 7.37 (7.38).

EXAMPLE 66

Ethyl 4-[6-acetyl-3-[3-(4-acetyl-3-hydroxy-2-propylphenoxy)propylsulfonyl]-2-propylphenoxy]butyrate Likewise as in Example 31, the title compound was obtained as pale yellow oil with yield of 58.4%.

Analysis (%) for $C_{31}H_{42}O_9S$, Calcd. (Found): C, 63.03 (63.14); H, 7.17 (7.19).

EXAMPLE 67

[4-(3-Bromopropylsulfinyl)-2-hydroxy-3-propylphenyl] ethanone

Likewise as in Example 31, the title compound was obtained as pale yellow oil with yield of 55.2%. Mass spectrum (m/z): 346 ($M^+$), 348 ($M^+$+2).

EXAMPLE 68

[4-(3 -Bromopropylsulfonyl)-2-hydroxy-3-propylphenyl] ethanone

Likewise as in Example 32, the title compound was obtained as yellow oil with yield of 63.4%. Mass spectrum (m/z): 362 ($M^+$), 364 ($M^+$+2).

EXAMPLE 69–71

Likewise as in Example 16 and 31, the compounds listed in Table 6 were synthesized.

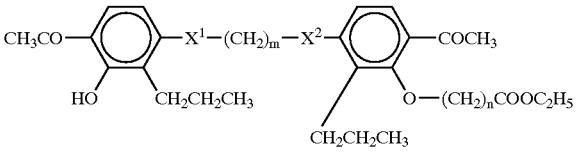

TABLE 6

| Ex. | $X^1$ | $X^2$ | m | n | Yield (%) | mp (° C.) | Analysis (%) | Calcd./ Found |
|---|---|---|---|---|---|---|---|---|
| 69 | SO | S | 3 | 3 | 69.9 | oil | C: 63.02 | H: 7.17 |
| | | | | | | | 63.03 | 7.16 |
| 70 | $SO_2$ | S | 3 | 3 | 77.8 | oil | C: 61.36 | H: 6.98 |
| | | | | | | | 61.44 | 6.98 |
| 71 | $SO_2$ | SO | 3 | 3 | 68.3 | oil | C: 59.78 | H: 6.80 |
| | | | | | | | 59.97 | 6.85 |

EXPERIMENT 1

Inhibition test of bronchoconstriction in guinea pig

Male Hartley guinea pig weighing about 450 g was anesthetized with sodium pentobarbital (30 mg/kg,i.p.), and the changes in transpulmonary pressure was measured according to the modified method of Konzett-Rössler (J. Harvey et al., J. Pharmacol. Method. 9, 147–155, 1983). Bronchoconstrictor response was induced by injection of leukotriene $D_4$ (3 μg/kg) into left jugular vein. Further, indomethacin and propranolol were injected into vein of the animal, prior to the injection of leukotriene $D_4$. Test compounds suspended in 5% solution of Gum Arabic were administered orally 2 hours before the injection of leukotriene $D_4$. The results of the Experiment are shown in Table 7.

TABLE 7

| Example | Dose (mg/kg, p.o.) | Inhibition |
|---|---|---|
| 33 | 3.125 | 28.0 |
| | 6.25 | 40.2 |
| | 12.5 | 63.9 |
| | 50 | 94.8 |
| 35 | 6.25 | 10.7 |
| | 12.5 | 51.3 |
| | 50 | 92.4 |
| 45 | 1.56 | 22.4 |
| | 3.125 | 54.2 |
| | 6.25 | 71.3 |
| | 12.5 | 72.7 |
| | 50 | 96.2 |
| 46 | 3.125 | 38.5 |
| | 6.25 | 46.6 |
| | 12.5 | 37.5 |
| | 50 | 94.2 |
| 47 | 3.125 | 29.1 |
| | 12.5 | 72.5 |
| | 50 | 92.9 |
| 48 | 3.125 | 33.6 |
| | 12.5 | 79.7 |
| | 50 | 90.7 |
| 49 | 6.25 | 19.1 |
| | 12.5 | 58.9 |
| | 50 | 77.7 |

TABLE 7-continued

| Example | Dose (mg/kg, p.o.) | Inhibition |
|---|---|---|
| 53 | 3.125 | 15.2 |
| | 6.25 | 50.4 |
| | 12.5 | 60.4 |
| | 50 | 66.7 |
| 55 | 6.25 | 36.4 |
| | 12.5 | 45.0 |
| | 50 | 88.0 |

What is claimed:

1. A phenoxyalkylcarboxylic acid derivative represented by the following general formula (I), (I)

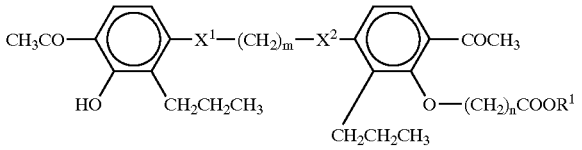

wherein $R^1$ indicates hydrogen atom, methyl group or ethyl group, m is an integer from 2 to 5, and n is an integer from 3 to 8, $X^1$ and $X^2$ each independently represent sulfur atom, oxygen atom, sulfinyl group or sulfonyl group, proviso $X^1$ and $X^2$ are not simultaneously oxygen atom; their alkali salt and hydrate.

*2. 4-[6-acetyl-3-[3-(4-acetyl-3-hydroxy-2-propylphenylthio)propoxy]-2-propylphenoxy]butyric acid.*

* * * * *